(12) United States Patent
Byrne et al.

(10) Patent No.: US 7,696,710 B2
(45) Date of Patent: Apr. 13, 2010

(54) METHOD OF SENSING AN AMOUNT OF MOISTURE ON A SURFACE OF A SUBSTRATE WITH TEMPERATURE COMPENSATION

(75) Inventors: Colin J. Byrne, Ypsilanti, MI (US);
Brent W. Pankey, Brighton, MI (US);
Mitchell Max Rohde, Saline, MI (US);
Karl Grosh, Ann Arbor, MI (US)

(73) Assignee: AGC Automotive Americas R&D, Inc., Ypsilanti, MI (US)

( * ) Notice: Subject to any disclaimer, the term of this patent is extended or adjusted under 35 U.S.C. 154(b) by 645 days.

(21) Appl. No.: 11/554,302

(22) Filed: Oct. 30, 2006

(65) Prior Publication Data
US 2008/0099042 A1 May 1, 2008

(51) Int. Cl.
*B60S 1/08* (2006.01)
(52) U.S. Cl. .................. 318/444; 318/480; 318/483
(58) Field of Classification Search .......... 318/443, 318/444, 480, 483
See application file for complete search history.

(56) References Cited

U.S. PATENT DOCUMENTS

| | | | |
|---|---|---|---|
| 4,180,886 A | 1/1980 | Scherz | |
| 4,495,452 A * | 1/1985 | Boegh-Peterson | ........... 318/444 |
| 4,542,325 A | 9/1985 | Kobayashi et al. | |
| 4,768,256 A | 9/1988 | Motoda | |
| 4,871,917 A * | 10/1989 | O'Farrell et al. | ......... 250/341.7 |
| 5,203,207 A | 4/1993 | Sugiyama | |
| 5,266,873 A | 11/1993 | Arditi et al. | |
| 5,360,268 A | 11/1994 | Hayashi et al. | |
| 5,432,415 A | 7/1995 | Ittah et al. | |
| 5,539,289 A | 7/1996 | Wiget | |
| 5,598,380 A | 1/1997 | Saurer et al. | |
| 5,682,788 A * | 11/1997 | Netzer | ........................ 73/73 |
| 5,818,341 A | 10/1998 | Saurer et al. | |
| 5,920,167 A | 7/1999 | Wiget et al. | |
| 5,990,647 A | 11/1999 | Zettler | |
| 6,015,449 A | 1/2000 | Hirota et al. | |

(Continued)

FOREIGN PATENT DOCUMENTS

EP     0598875 B1     6/1994

(Continued)

OTHER PUBLICATIONS

U.S. Appl. No. 11/554,265, Title: Ultrasonic Phase Shift Moisture Sensing System With Temperature Compensation; Filing date Oct. 30, 2006.

(Continued)

*Primary Examiner*—Bentsu Ro
(74) *Attorney, Agent, or Firm*—Howard & Howard Attorneys PLLC (57) ABSTRACT

A method for determining an amount of moisture on a surface of a substrate includes a step of transmitting a transmitter signal to generate a wave. The transmitter signal has a first phase. The wave is propagated to vibrate the surface. Vibrations in the surface are detected and converted into a receiver signal. The receiver signal has a second phase different than the first phase. The method includes the step of sensing the temperature of the substrate. The amount of moisture on the surface is computed based on a phase shift between the transmitter signal and the receiver signal that has been compensated to account for surface temperature.

24 Claims, 6 Drawing Sheets

U.S. PATENT DOCUMENTS

| | | | |
|---|---|---|---|
| 6,232,603 B1 | 5/2001 | Nelson | |
| 6,422,062 B1 | 7/2002 | King et al. | |
| 6,634,225 B1 * | 10/2003 | Reime | 73/170.17 |
| 6,888,465 B2 | 5/2005 | Schmitt et al. | |
| 6,936,985 B2 * | 8/2005 | Pankey et al. | 318/443 |
| 7,095,199 B2 * | 8/2006 | Hirose et al. | 318/444 |
| 7,204,130 B2 * | 4/2007 | Koram et al. | 73/73 |
| 7,296,461 B2 * | 11/2007 | Barguirdjian et al. | 73/73 |
| 2003/0192566 A1 | 10/2003 | Neubauer et al. | |

FOREIGN PATENT DOCUMENTS

| | | | |
|---|---|---|---|
| EP | 0723897 A1 | 7/1996 | |
| EP | 0610132 A1 | 12/1997 | |
| JP | 62127689 | 6/1987 | |
| JP | 05142356 | 8/1993 | |
| WO | WO9400319 A1 | 1/1994 | |
| WO | WO02055352 A1 | 7/2002 | |

OTHER PUBLICATIONS

English language Abstract for EP0598875 extracted from esp@cenet.com, dated Oct. 30, 2006.

English language Abstract for EP0723897 extracted from esp@cenet.com, dated Oct. 30, 2006.

English language Abstract for EP0810132 extracted from esp@cenet.com, dated Oct. 30, 2006.

English language Abstract for JP05142356 extracted from Japanese Patent Office.

English language Abstract for JP62127689 extracted from esp@cenet.com, dated Oct. 30, 2006.

English language Abstract for WO9400319 extracted from esp@cenet.com, dated Oct. 30, 2006.

English language Abstract for WO02055352 extracted from esp@cenet.com, dated Oct. 30, 2006.

* cited by examiner

FIG - 10

METHOD OF SENSING AN AMOUNT OF MOISTURE ON A SURFACE OF A SUBSTRATE WITH TEMPERATURE COMPENSATION

BACKGROUND OF THE INVENTION

1. Field of the Invention

The present invention generally relates to a method for sensing an amount of moisture on a surface.

2. Description of the Related Art

Various methods for sensing an amount of moisture on a surface are known in the art. One such method is shown in U.S. Pat. No. 5,432,415 (the '415 patent). To sense moisture on the surface of a window, the method of the '415 patent includes a step of transmitting a transmitter signal having a first phase to generate a wave. The method continues with a step of propagating the wave along the window to a receiver to vibrate the window. The method next includes a step of converting the wave into a receiver signal having a second phase. Since the amount of moisture on the window corresponds to variation in the second phase relative to the first phase, the method of the '415 patent includes a step of comparing the first phase to the second phase. Once compared, the method includes a step of comparing the difference between the first phase and the second phase to a threshold value. The threshold value represents a minimum amount of moisture on the windshield necessary to enable the wiper system. The method further includes a step of actuating a wiper system to remove the moisture from the surface if the difference between the first phase and the second phase exceeds the threshold value.

Although the sensing system of the '415 patent can provide an approximation of moisture on the surface, it lacks the ability to finely sense the amount of moisture on the surface because it does not incorporate the ability to compensate for factors that affect phase shift other than moisture by accounting for factors other than moisture. An example of such a factor is the temperature of the window. If not properly incorporated in the moisture estimation system calculation, the temperature of the window may cause either a "false positive" for moisture on the surface and needlessly operate the wipers or a "false negative" and not operate the wipers when there is moisture on the surface. Hence, there remains an opportunity for a method of determining the amount of moisture on the surface that compensates for the temperature of the surface in determining the amount of moisture on the surface and thus yields a more robust system.

SUMMARY OF THE INVENTION AND ADVANTAGES

The subject invention provides a method of determining an amount of moisture on a surface. The method includes the steps of transmitting a transmitter signal to generate a vibrational wave and propagating the vibrational wave to vibrate the substrate. The method continues by detecting the vibrations of the substrate and converting the vibrations into a receiver signal. The temperature of the substrate is sensed. The method further includes a step of compensating for a phase shift between the transmitter signal and the receiver signal attributable to the temperature of the substrate to determine the amount of moisture on the surface.

Accordingly, the method of the subject invention compensates for the phase shift attributable to the temperature of the substrate and thus provides a more accurate measure of the amount of moisture on the substrate. When the method of the subject invention is used with a vehicle wiper system, greater accuracy permits the method of the subject invention to enable the wiper system in response to the amount of moisture on the surface independent of the temperature of the substrate.

BRIEF DESCRIPTION OF THE DRAWINGS

Other advantages of the present invention will be readily appreciated, as the same becomes better understood by reference to the following detailed description when considered in connection with the accompanying drawings wherein.

DETAILED DESCRIPTION OF THE INVENTION

Referring to the Figures, wherein like numerals indicate corresponding parts throughout the several views, a sensing system 10 for sensing an amount of moisture 12 on an outer surface 14 of a substrate 16 is shown.

Figure 1:
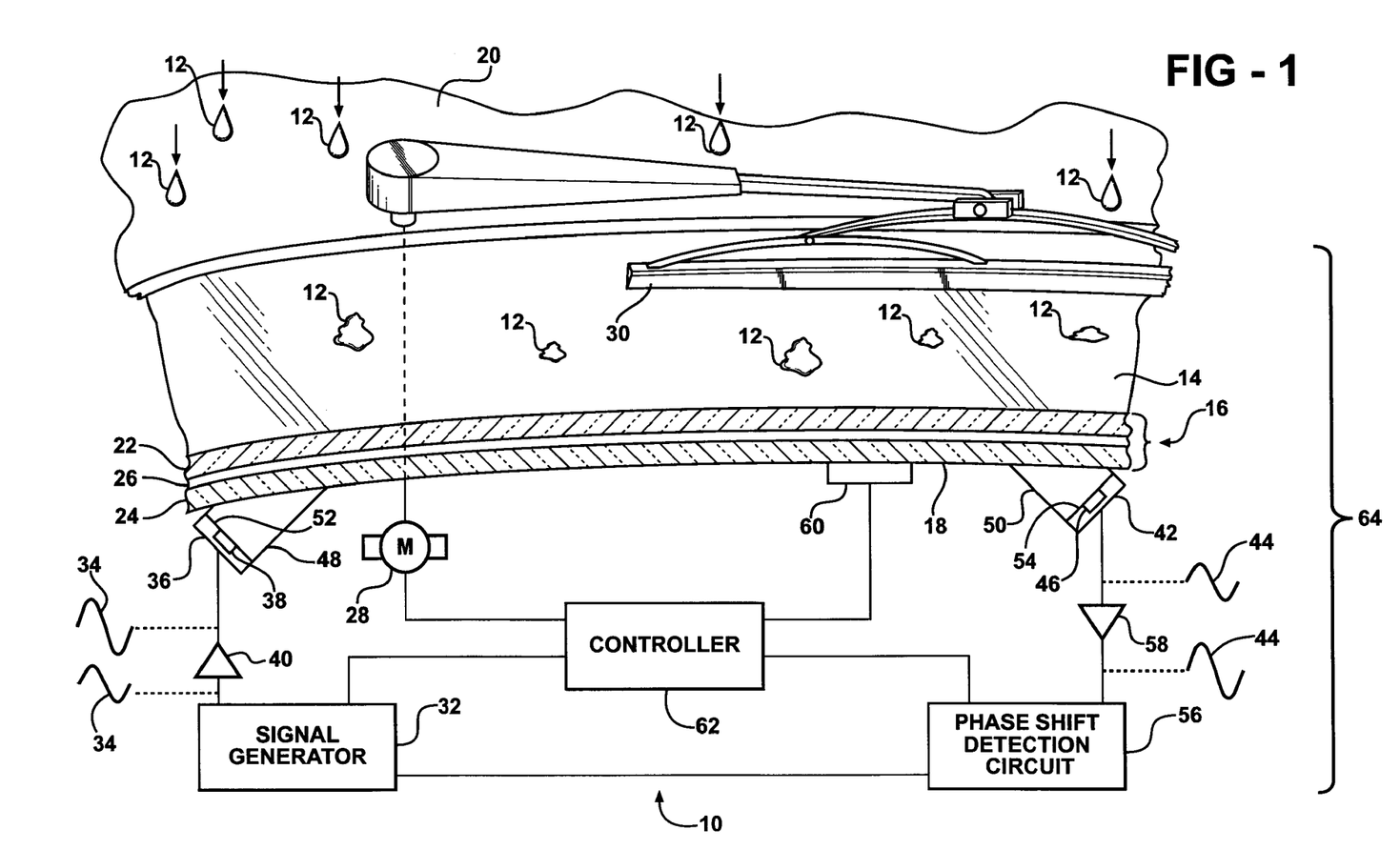
FIG. 1 is a combination block diagram and partial cross-sectional view of a preferred embodiment of a sensing system showing electrical and communicative connections between the various devices, connection of a transmitter and a receiver to a windshield of a vehicle, and connection to a wiper blade for wiping the windshield.
Figure 2:
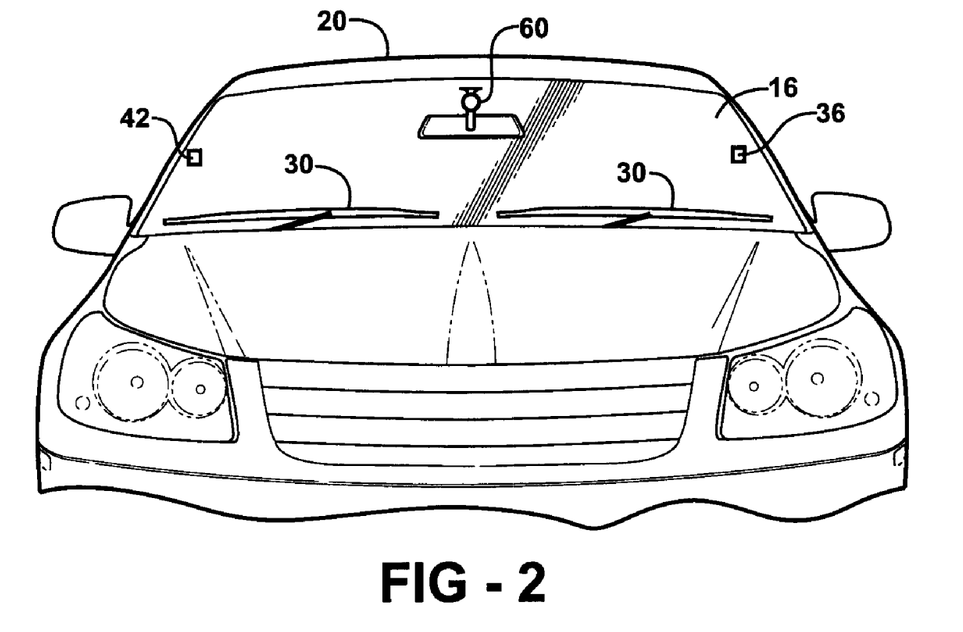
FIG. 2 is a front view of the vehicle showing the windshield with the transmitter and receiver mounted at opposite sides of the windshield mid-way between a top and a bottom.
Figure 3:
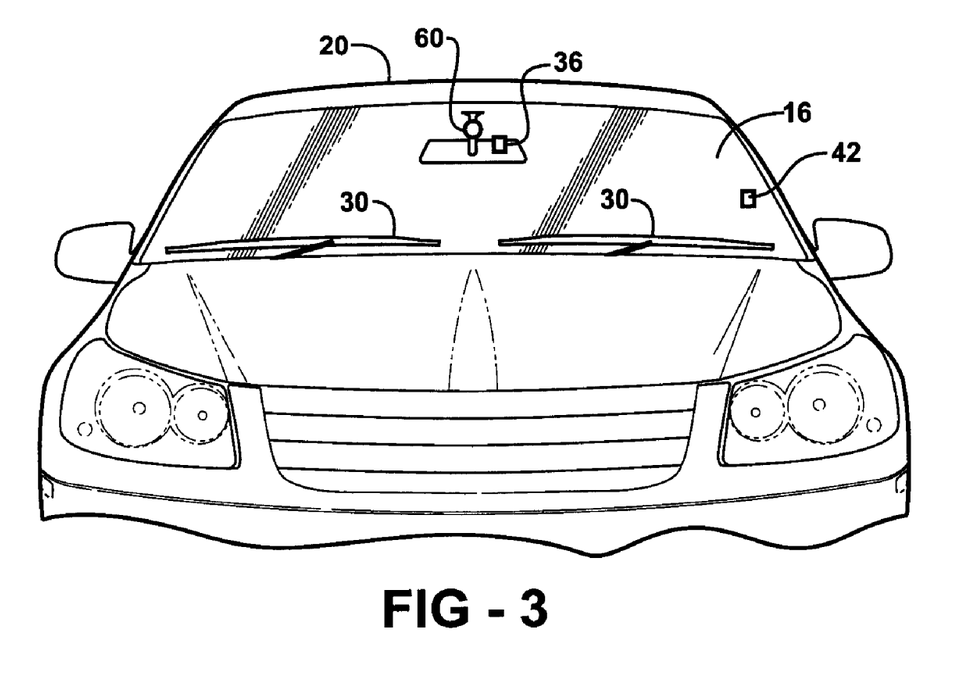
FIG. 3 is a front view of the vehicle with the transmitter mounted at a top and center of the windshield and the receiver mounted near a driver's side mid-way between the top and bottom.
Figure 4:
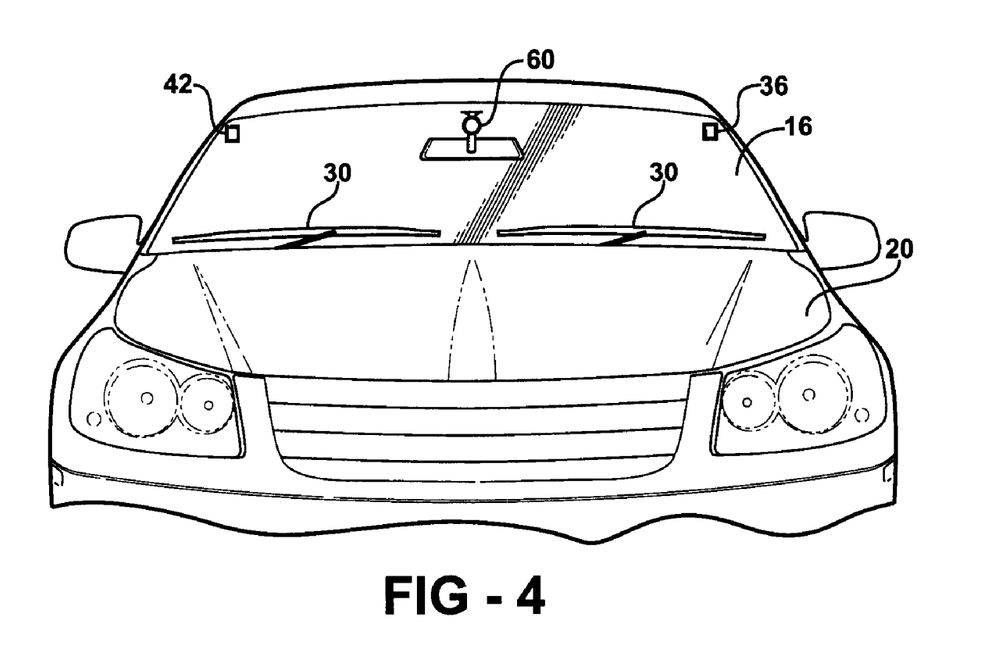
FIG. 4 is a front view of the vehicle with the transmitter and receiver mounted at opposite sides of the windshield near the top.
Figure 5:
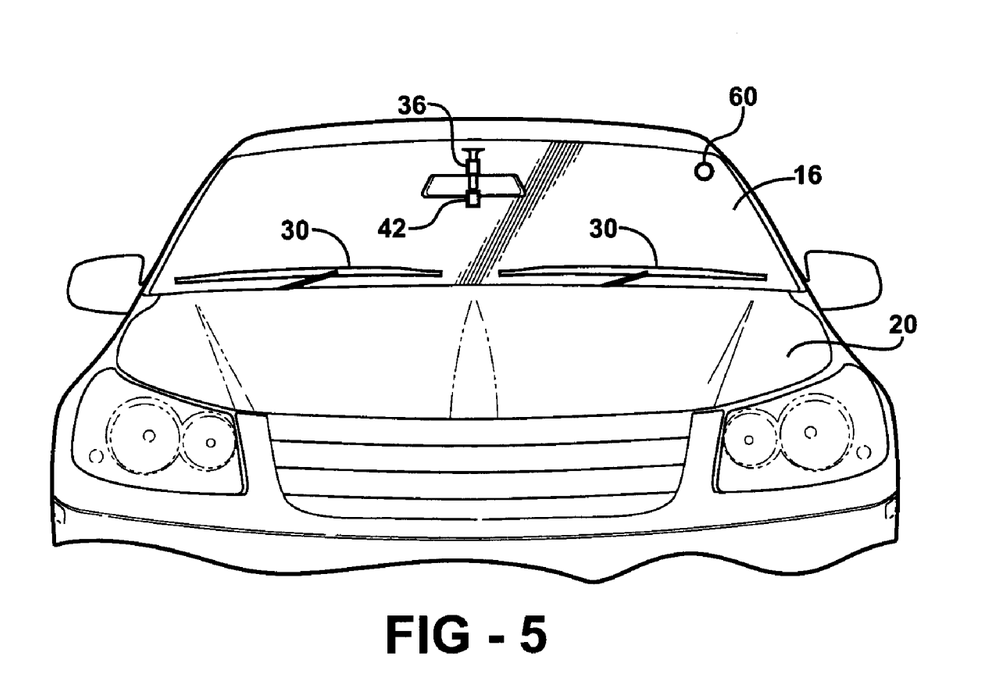
FIG. 5 is a front view of the vehicle with the transmitter and receiver mounted at a top and center of the windshield.

Referring to FIG. 1, the substrate 16 defines an inner surface 18 and an outer surface 14. In a preferred embodiment, the substrate 16 is further defined as at least one pane of glass and is commonly referred to as a window glazing. As shown in FIG. 2, the substrate 16 may be incorporated as part of a vehicle 20. The outer surface 14 of the substrate 16 generally faces the outside of the vehicle 20, i.e., the side that exposed to the elements, such as rain or snow. The inner surface 18 of the substrate 16 generally faces the inside of the vehicle 20, i.e., the passenger compartment. Of course, the terms inner surface 18 and outer surface 14 are used merely for convenience and could be reversed as is realized by those skilled in the art.

Those skilled in the art also appreciate that the substrate 16 may be incorporated in the vehicle 20 as a windshield, a back window, a side window, a sun roof, etc. In the case of the back window or the side window, the substrate 16 is typically a single pane of glass. For a windshield, the substrate 16 is typically a first pane of glass 22 and a second pane of glass 24 sandwiching a transparent polymer layer 26, such as polyvinyl butyral (PVB). Preferably, the panes of glass 22, 24 are further defined generally as automotive glass, and more specifically as soda-lime-silica glass. Those skilled in the art also appreciate that materials, other than glass, may be used to form the substrate 16, e.g., resin, polycarbonate, acrylic, etc.

The sensing system 10 of the preferred embodiment may also include a wiper system having a wiper motor 28. The wiper system may also include at least one wiper blade 30 operatively connected to the wiper motor 28. When the wiper motor 28 is actuated, the wiper blade(s) 30 move across the substrate 16 to remove the moisture 12 (and other foreign objects, such as dust, dirt, etc.) from the substrate 16. The wiper system may include a plurality of operating levels that correspond to a speed of the wiper motor 28 and the wiper blades 30 and/or an interval of time between actuation of the wiper blades 30.

The sensing system 10 includes a signal generator 32 for generating a transmitter signal 34. Preferably, the signal generator 32 generates a sinusoidal waveform, however, those skilled in the art realize that other waveforms, such as triangular waves, square waves, or saw tooth waves, may also be generated. The transmitter signal 34 preferably has a frequency in the ultrasonic range. The frequency of the transmitter signal 34 may be determined based on the size and composition of the substrate and other factors. The frequency is preferably greater than 20 kHz, which is the upper range of human hearing, and more preferably in the range of 100 to 1,200 kHz. However, those skilled in the art realize other frequencies, including those in an audible range (between 20-20,000 Hz) may also be utilized. The transmitter signal 34 may be pulsed, i.e., turned on and off, or continuous, i.e., always on.

A transmitter 36 is electrically connected to the signal generator 32 for producing a wave corresponding to the transmitter signal 34. The transmitter 36 is operatively connected to the inner surface 18 of the substrate 16 such that the wave propagates through the substrate 16. This propagation of the wave causes the substrate 16 to vibrate, although imperceptible to human senses. In the preferred embodiment, the transmitter 36 includes a transmitting piezoelectric element 38. The transmitting piezoelectric element 38 physically actuates in response to the transmitter signal 34 to generate the wave in the substrate 16. Of course, those skilled in the art realize other techniques for generating the wave in the substrate 16, apart from piezoelectrics.

Also in the preferred embodiment, a transmitter amplifier 40 is electrically connected between the signal generator 32 and the transmitter 36 for amplifying the transmitter signal 34. Those skilled in the art realize that the transmitter amplifier 40 may be a component separate from the signal generator 32 or may be integrated with either the signal generator 32 or the transmitter 36. Furthermore, the signal generator 32, transmitter amplifier 40, and transmitter 36 may be integrated together in a single unit.

A receiver 42 is operatively connected to the inner surface 18 of the substrate 16 and spaced apart from the transmitter 36. The receiver 42 receives the wave produced by the transmitter 36. The receiver 42 generates a receiver signal 44 corresponding to the received wave. In the preferred embodiment, the receiver 42 includes a receiving piezoelectric element 46. When actuated, the receiving piezoelectric element 46 generates the receiver signal 44. As with the transmitter 36, those skilled in the art realize other techniques to generate the receiver signal 44, apart from piezoelectrics. Those skilled in the art also realize that the transmitter 36 and the receiver 42 may each be a transducer, capable of transmitting or receiving. Thus, the transmitter 36 and receiver 42 may be an identical device, but simply operated in a different way.

The sensor system 10 may also include a transmitter coupler component 48 and a receiver coupler component 50. The transmitter coupler component 48 is disposed between the transmitter 36 and the inner surface 18 of the substrate 16 and the receiver coupler component 50 is disposed between the inner surface 18 of substrate 16 and the receiver 42. The transmitter coupler component 48 separates the transmitter 36 from the substrate 16 while allowing propagation of the wave from the transmitter 36 to the substrate 16. Likewise, the receiver coupler component 50 separates the receiver 42 from the substrate 16 while allowing propagation of the wave from the substrate 16 to the receiver 42. In the preferred embodiment, the coupler components 48, 50 are formed of acrylic, however other suitable materials for allowing wave propagation may also be utilized.

The transmitter coupler component 48 includes a first directing surface 52 angled relative toward the receiver 42 for directing the transmitter 36 toward the receiver 42. Likewise, the receiver coupler component 50 includes a second directing surface 54 angled relative toward the transmitter 36 for directing the receiver 42 toward the transmitter 36. Angling of the transmitter 36 and the receiver 42 towards one another results in better propagation of the wave from the transmitter 36 and better reception of the wave by the receiver 42. In the preferred embodiment, each coupler component 48, 50 has a wedge shape. The angle of the first and second directing surfaces 52, 54 is preferably in the range of 10-45 degrees from a line that is parallel to the inner surface 18 of the substrate 16. The angle off the first and second directing surfaces 52, 54 is based, in part, by the dimensions of the substrate 16, the distance between the coupler components 48, 50, the composition of the substrate 16, and the composition of the coupler components 48, 50. Preferably, the angles of the first and second directing surfaces 52, 54 are about identical. The transmitter and receiver coupler components 48, 50 set the phase velocity of the wave, compensate for thermal expansion of the substrate 16, and provide impedance matching. Furthermore, those skilled in the art realize other functions performed by the coupler components 48, 50.

As shown in FIGS. 2-5, the transmitter 36 and receiver 42 may be disposed in any of several locations on the substrate 16. Obviously, the examples shown in FIGS. 2-5 are not inclusive of all possible locations for the transmitter 36 and receiver 42. Numerous factors must be considered in determining the location of the transmitter 36 and receiver 42. These factors include, but are not limited to, a coverage area of the wiper blades 30, potential obstruction of a view of a driver of the vehicle 20, the frequency and amplitude of the transmitter signal 34 and wave, the material and thickness of the substrate 16, the dimensions of the piezoelectric elements 38, 46, and the dimensions of the coupler components 48, 50.

Referring again to FIG. 1, a phase shift detection circuit 56 is electrically connected to the receiver 42 and the signal generator 32. This phase shift detection circuit 56 measures a phase shift between the transmitter signal 34 and the receiver signal 44. In the preferred embodiment, a receiver amplifier 58 is electrically connected between the receiver 42 and the phase shift detection circuit 56 for amplifying the receiver signal 44. Of course, the receiver amplifier 58 may be integrated within the receiver 42 or the phase shift detection circuit 56.

Figure 6:
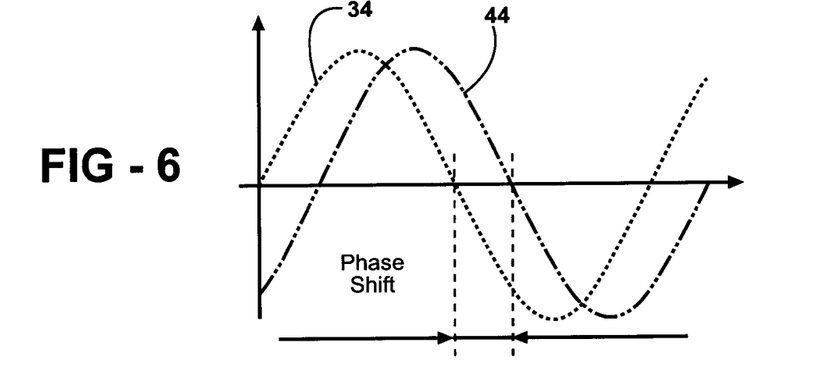
FIG. 6 is a graph showing a phase shift between a transmitter signal and a receiver signal.

Referring to FIG. 6, the phase shift between the transmitter signal 34 and the receiver signal 44 may be affected by a number of factors. These factors include the composition of the substrate and the distance between the transmitter and the receiver. Another factor is the presence of moisture 12 (or other foreign objects) on the substrate 16. The more moisture 12 on the substrate 16, the greater the phase shift between the transmitter signal 34 and the receiver signal 44. Thus, the amount of moisture 12 on the substrate 16 may be determined by calculating the phase shift between the transmitter signal 34 and the receiver signal 44.

Another factor that affects the phase shift is the temperature of the substrate 16. This significant factor could, if not taken into account, adversely disrupt any calculation of the moisture 12 on the substrate 16 based on the phase shift between the transmitter signal 34 and the receiver signal 44. The temperature of the substrate 16 affects the phase shift in a reliable and repeatable way, thus allowing its affects to be compensated for.

Therefore, the sensor system 10 of the present invention also includes a temperature sensor 60 for sensing a temperature of the substrate 16. Numerous acceptable temperature sensors 60 are known to those skilled in the art, including thermocouples and resistance temperature detectors (RTDs), which may be operatively connected to the substrate 16, or infrared techniques, which may not require a connection to the substrate 16.

The sensor system 10 also includes a controller 62 in communication with the phase shift detection circuit 56 and the temperature sensor 60. The controller 62 determines the amount of moisture 12 on the surface based on the measured phase shift and the temperature of the substrate 16. Calculating the amount of moisture 12 on the surface is performed by analyzing the phase shift and then compensating for the temperature of the substrate 16. In the preferred embodiment, the controller 62 is a microprocessor-based device, such as a microcontroller, running a software program. Of course, other suitable controllers 62 may be utilized as known to those skilled in the art.

The wiper motor 28 is preferably in communication with the controller 62. The controller 62 may activate the wiper motor 28 based on the amount of moisture 12 sensed on the outer surface 14 of the substrate 16. Specifically, the controller 62 will activate the wiper motor 28 if the amount of moisture 12 meets specific criteria. In the preferred embodiment, the wiper motor 28 is activated if the amount of moisture is greater than a threshold level. The threshold level is predetermined and stored in a memory storage device (not shown) of the controller 62. The threshold level may be set by a user, be adaptive, or permanently fixed.

A window assembly 64 may be formed by the combination of the substrate 16 and the sensing system 10. The various components 48, 50 of the sensing system 10, particularly the transmitter 36, the receiver 42, the temperature sensor 60, the transmitter coupler component 48, the transmitter 36 receiver 42 component, the amplifiers 40, 58, the phase shift detection circuit 56, the controller 62, and the signal generator 32, may all be supported by the substrate 16. Specifically, a circuit board (not shown) may support the phase shift detection circuit 56, the controller 62, the signal generator 32, and the amplifiers 40, 58, and provide electrical interconnections for these devices. The circuit board may then be attached to the substrate 16. However, those skilled in the art realize other suitable locations for the circuit board and techniques for electrically interconnecting the devices.

Figures 7, 8:
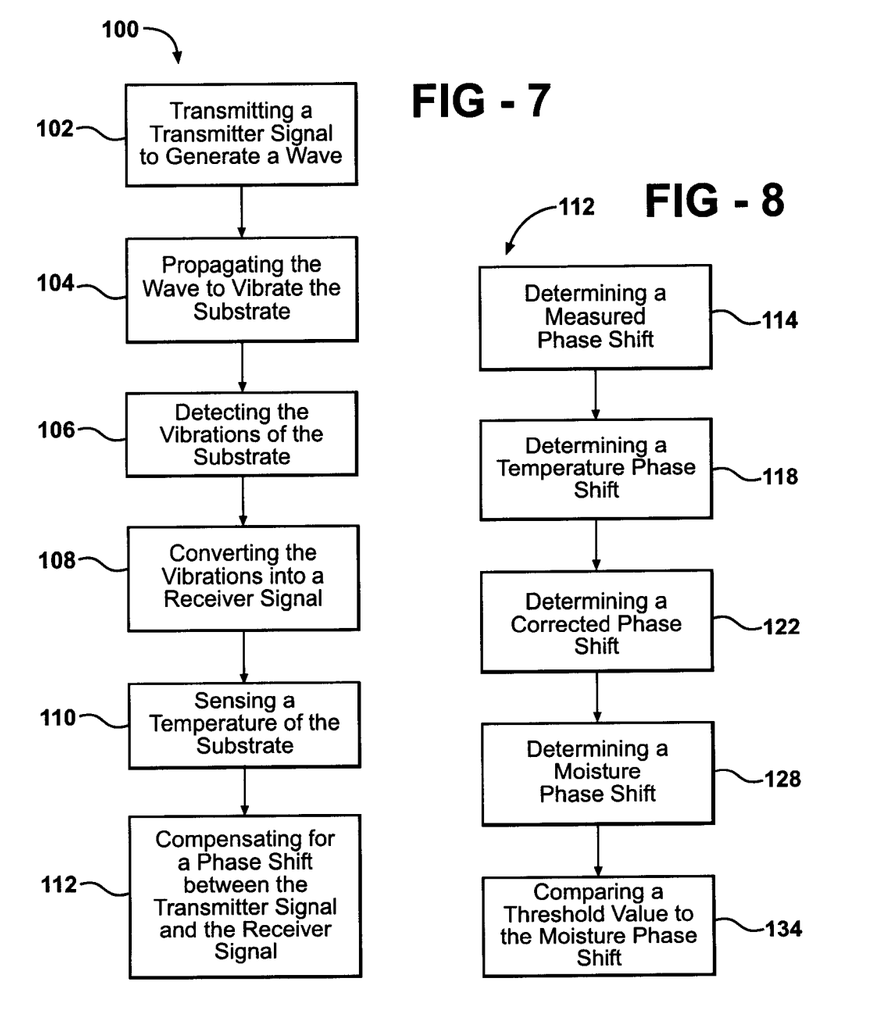
FIG. 7 is a flowchart of a method of sensing an amount of moisture on a surface of a substrate.
FIG. 8 is a flowchart illustrating steps of compensating for the phase shift attributable to the temperature of the substrate.
Figure 9:
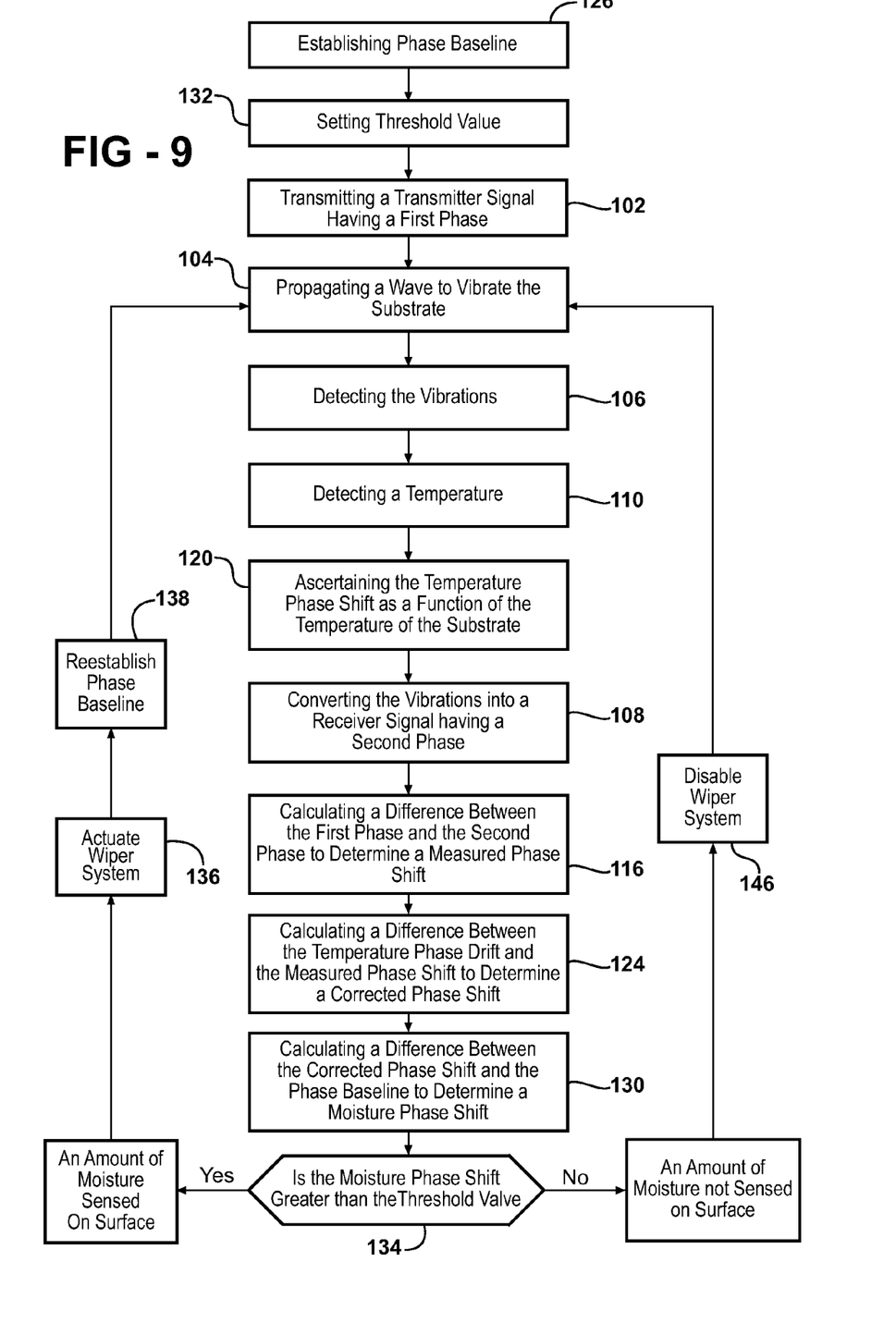
FIG. 9 is a flowchart illustrating steps of sensing an amount of moisture on the surface of the substrate and a method of removing the moisture from the surface.

Referring now to FIGS. 7-9, the subject invention includes a method 100 of determining the amount of moisture 12 on the surface 14 of the substrate 16. In a first step, the method includes a step 102 of transmitting the transmitter signal 34 to generate the wave. As described above, the transmitter signal 34 is generated by the signal generator 32. The transmitter 36 then transmits the transmitter signal 34 to the transmitter piezoelectric element 38. The method continues with a step 104 of propagating the wave through the substrate 16 to vibrate the substrate 16. Exciting the transmitter piezoelectric element 38 causes the wave to propagate along the substrate 16. Those skilled in the art realize that the vibrations of the substrate 16 are minute and typically not visible or otherwise perceptible to human senses. Accordingly, the method includes a step 106 of detecting the vibrations of the substrate 16. As the substrate 16 vibrates, the receiving piezoelectric element 46 detects the vibrations. Once detected, the method includes a step 108 of converting the vibrations into the receiver signal 44. In the preferred embodiment, the receiving piezoelectric element 46 converts the vibrations of the substrate 16 to the receiver signal 44.

The transmitter signal 34 has a first phase and the receiver signal 44 has a second phase. As shown in FIG. 6, the second phase is different from the first phase. This difference, i.e., the phase shift, is primarily due to the substrate 16 itself, moisture 12 on the surface 14 of the substrate 16, and the temperature of the substrate 16. Although other factors may cause the phase shift, the amount of moisture 12 and the temperature are the most significant variable factors. Referring back to FIGS. 7-10, in order to eliminate the phase shift based on temperature, the method includes a step 110 of determining the temperature of the substrate 16. In a preferred embodiment, the temperature sensor 60 senses the temperature of the substrate 16. With the temperature of the substrate 16, the controller 62 may compensate for a variation in the phase shift attributable to the temperature of the substrate 16. Therefore, the method includes a step 112 of compensating for the phase shift between the transmitter signal and the receiver signal attributable to the temperature of the substrate 16 to determine the amount of moisture 12 on the surface 14.

The step 112 of compensating for the phase shift attributable to temperature is further defined by several steps. First, the method includes a step 114 of determining a measured phase shift. The measured phase shift corresponds to the variance in the second phase relative to the first phase. In other words, the measured phase shift represents the difference between the first phase and the second phase caused by the amount of moisture 12 on the surface 14, the temperature of the substrate 16, the substrate 16 itself, or other factors. As such, the measured phase shift may be determined by a step 116 of calculating a difference between the first phase and the second phase, i.e., calculating the phase shift between the transmitter signal 34 and the receiver signal 44. In a preferred embodiment, the phase shift detection circuit 56 is used to determine the measured phase shift.

Next, the step 112 of compensating includes a step 118 of determining a temperature phase shift. The temperature phase shift is the variation in the second phase relative to the first phase that is attributable to the temperature of the substrate 16. In order to determine the temperature phase shift, the method includes a step 120 of ascertaining the temperature phase shift as a function of the temperature of the substrate 16. Several techniques may be employed to ascertain the temperature phase shift. One technique is to utilize a formula that can be solved for temperature phase shift when the temperature of the substrate 16 is provided. Another technique is to employ a "look-up" table that contains a plurality of temperature phase shift values with each temperature phase shift value correlated with a substrate 16 temperature value. Accordingly, the method may include a step of storing the temperature phase shift as a function of the temperature of the substrate 16 in the table of the memory storage device. In order to access the temperature phase shift, the method may further include a step of retrieving the temperature phase shift from the table.

Furthermore, the method includes a step 122 of determining a corrected phase shift attributable to the amount of moisture 12 on the surface 14 independent of the temperature of the substrate 16. Determining the corrected phase shift may be further defined as a step 124 of calculating a difference between the temperature phase shift and the measured phase shift. In other words, in a preferred embodiment, the corrected phase shift represents the measured phase shift independent of the temperature phase shift. In a preferred embodiment, the controller is 62 automatically determines the corrected phase shift by calculating the difference between the temperature phase shift and the measured phase shift.

As previously discussed, various factors may affect the variation in the measured phase shift. Besides moisture 12 on the surface 14 of the substrate 16 and the temperature of the substrate 16, the substrate 16 itself causes a phase shift. Therefore, the method includes a step 126 of establishing a phase baseline corresponding to the measured phase shift independent of the amount of moisture 12 on the surface 14 and the temperature of the substrate 16. The phase baseline represents the status of the surface 14 following a wipe. This phase baseline is the adaptive reference point of the condition.

Additionally, the method includes a step 128 of determining a moisture phase shift attributable to the amount of moisture 12 on the surface 14 independent of the temperature of the substrate 16 and the phase baseline. Determining the moisture phase shift may be further defined as a step 130 of calculating a difference between the corrected phase shift and the phase baseline. Accordingly, the moisture phase shift corresponds to the phase shift independent of the temperature of the substrate 16 to sense the amount of moisture 12 on the surface 14. In a preferred embodiment, the controller 62 automatically determines the moisture phase shift by calculating the difference between the corrected phase shift and the phase baseline.

Furthermore, the method includes a step 132 of setting a threshold value. The threshold value represents a tolerance of the minimum amount of moisture 12 permitted on the surface 14. Once the threshold value is set, the method includes a step 134 of comparing the moisture phase shift to the threshold value. In a preferred embodiment, the controller 62 automatically compares the moisture phase shift to the threshold value. The threshold value may be adjusted by the user, adaptively set by the controller 62, and/or fixed at a constant point.

In addition to sensing the amount of moisture 12 on the surface 14, the method of the subject invention may further include steps for removing moisture 12 from the surface 14 of the substrate 16 with the wiper motor 28 and the wiper blade 30. In a preferred embodiment, the method of the subject invention is used with the wiper system. As previously described, the method includes steps for determining the amount of moisture 12 on the surface 14 of the substrate 16 phase shift corresponding to at least one of the amount of moisture 12 on the surface 14 and a temperature of the substrate 16. The method includes a step 136 of actuating the wiper system in response to the variation in the second phase relative to the first phase to remove the moisture 12 from the surface 14 of the substrate 16. Specifically, if the moisture phase shift exceeds the threshold value, the method includes the step 136 of actuating the wiper system to remove the moisture 12 from the surface 14 of the substrate 16. In order to actuate the wiper system, the controller 62 enables the wiper motor 28, and the wiper motor 28 moves the wiper blade(s) 30 across the surface 14 of the substrate 16. The wiper blade 30 pushes moisture 12 from the surface 14, effectively reducing the amount of moisture 12 on the surface 14. Once the wiper system has been actuated, the method further includes a step 138 of reestablishing the phase baseline The phase baseline is reestablished due to temperature change of the substrate 16 and/or residual moisture 12 left on the surface 14 of the substrate 16 after actuation of the wiper blade(s) 30.

Figure 10:
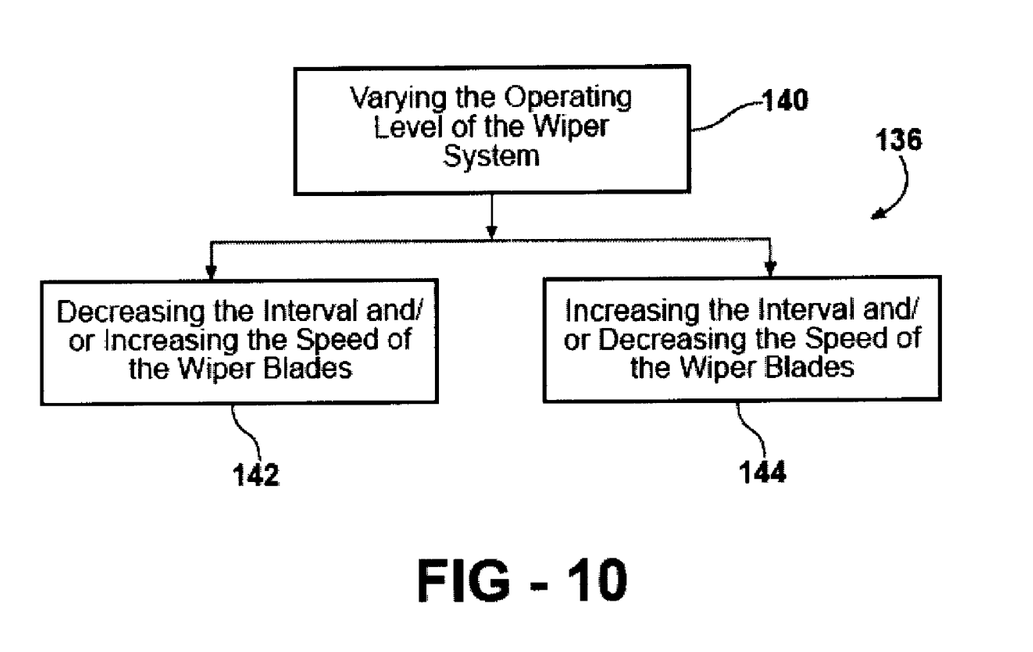
FIG. 10 is a flowchart illustrating steps of actuating a wiper system to remove the moisture from the surface.

Referring now to FIG. 10, the step 136 of actuating the wiper system includes a step 140 of varying the operating level of the wiper system based on the amount of moisture 12 sensed. It is advantageous to either decrease the interval of time between actuation of the wiper blades 30 or increase the speed of the wiper blades 30, as the amount of moisture 12 on the substrate 16 increases. Consequently, the method includes a step 142 of increasing the operating level of the wiper system in response to the amount of moisture on the surface 14. Specifically, as the amount of moisture 12 on the substrate 16 increases, the operating level increases. In a preferred embodiment, the controller 62 enables the wiper motor 28 to decrease the interval of time between actuation of the wiper blades 30 and/or increase the speed of the wiper blades 30 as the amount of moisture 12 on the surface 14 increases.

Likewise, it is advantageous to increase the interval of time between actuation of the wiper blades or decrease the speed of the wiper blades 30, as the amount of moisture 12 on the substrate 16 decreases. Consequently, the method includes a step 144 of decreasing the operating level of the wiper system in response to the amount of moisture on the surface 14. Specifically, as the amount of moisture 12 on the substrate 16 decreases, the operating level decreases. In a preferred embodiment, the controller 62 enables the wiper motor 28 to increase the interval of time between actuation of the wiper blades 30 and/or decrease the speed of the wiper blades 30 as the amount of moisture 12 on the surface 14 decreases.

Similarly, it is advantageous to disable the wiper system once the moisture phase shift fails to exceed the threshold value, thus indicating little or no moisture 12 on the surface 14 of the substrate 16. Accordingly, the method includes a step 146 of disabling the wiper system in response to the amount of moisture on the surface 14. Specifically, if the moisture phase shift fails to exceed the threshold value, the wiper system is disabled. In a preferred embodiment, the controller 62 disables the wiper motor 28 when the moisture phase shift fails to exceed the threshold value, thus preventing the wiper blade 30 from moving across the surface 14. The controller 62 may further control the wiper motor 28 to return the wiper blade 30 to a resting position when the moisture phase fails to exceed the threshold value.

The method described herein yields improved moisture sensing on a surface 14 by compensating for the phase shift attributable to the temperature variation of the substrate 16. Accordingly, the subject method provides a more accurate measure of the amount of moisture 12 on the substrate 16. When used with a wiper system, the method enables the wiper system in response to the amount of moisture on the surface independent of the temperature of the substrate.

Obviously, many modifications and variations of the present invention are possible in light of the above teachings. The invention may be practiced otherwise than as specifically described within the scope of the appended claims.

What is claimed is:

1. A method of determining an amount of moisture on a surface of a substrate, said method comprising the steps of:

transmitting a transmitter signal to generate a vibrational wave;

propagating the vibrational wave to vibrate the substrate;

detecting the vibrations of the substrate;
convening the vibrations into a receiver signal;
sensing the temperature of the substrate; and
compensating for a phase shift between the transmitter signal and the receiver signal attributable to the temperature of the substrate to determine the amount of moisture on the surface;
wherein said step of compensating includes determining a measured phase shift corresponding to at least one of the amount of moisture on the surface and the temperature of the substrate;
wherein said step of compensating includes determining a temperature phase shift attributable to the temperature of the substrate;
wherein said step of determining the temperature phase shift includes ascertaining the temperature phase shift as a function of the temperature of the substrate; and
wherein said step of determining the temperature phase shift includes storing the temperature phase shift as a function of the temperature of the substrate in a table.

2. A method as set forth in claim 1 wherein said step of determining the measured phase shift is further defined as calculating a difference between a first phase of the transmitter signal and a second phase of the receiver signal.

3. A method as set forth in claim 1 wherein said step of determining the temperature phase shift includes retrieving the temperature phase shift from the table.

4. A method as set forth in claim 1 wherein said step of compensating includes determining a corrected phase shift attributable to the amount of moisture on the surface independent of the temperature of the substrate.

5. A method as set forth in claim 4 wherein said step of determining the corrected phase shift is further defined as calculating a difference between the temperature phase shift and the measured phase shift.

6. A method as set forth in claim 4 wherein said step of compensating includes establishing a phase baseline corresponding to the measured phase shift independent of the amount of moisture on the surface and the temperature of the substrate.

7. A method as set forth in claim 6 wherein said step of compensating includes determining a moisture phase shift attributable to the amount of moisture on the surface independent of the temperature of the substrate and the phase baseline.

8. A method as set forth in claim 7 wherein said step of determining the moisture phase shift is further defined as calculating a difference between the corrected phase shift and the phase baseline.

9. A method as set forth in claim 7 wherein said step of compensating includes setting a threshold value corresponding to a minimum measured phase shift independent of the amount of moisture on the surface and the temperature of the substrate.

10. A method as set forth in claim 9 wherein said step of compensating includes comparing the moisture phase shift to the threshold value.

11. A method as set forth in claim 10 further including a wiper system and wherein said method includes a step of actuating the wiper system if the moisture phase shift exceeds the threshold value.

12. A method as set forth in claim 10 wherein said step of compensating includes reestablishing the phase baseline if the moisture phase shift exceeds the threshold value.

13. A method as set forth in claim 10 further including a wiper system and wherein said method includes a step of disabling the wiper system if the moisture phase fails to exceed the threshold value.

14. A method as set forth in claim 1 further including a wiper system and said method includes a step of actuating the wiper system in response to the amount of moisture on the surface.

15. A method as set forth in claim 14 wherein the wiper system includes a plurality of operating levels corresponding to a speed of the wiper system and wherein said step of actuating includes varying the operating level of the wiper system in response to the amount of moisture on the surface.

16. A method as set forth in claim 15 wherein step of varying is further defined as increasing the operating level of the wiper system in response to the amount of moisture on the surface.

17. A method as set forth in claim 15 wherein said step of varying is further defined as decreasing the operating level of the wiper system in response to the amount of moisture on the surface.

18. A method as set forth in claim 1 further including a wiper system and said method includes a step of disabling the wiper system in response to the amount of moisture on the surface.

19. A method of determining an amount of moisture on a surface of a substrate, said method comprising the steps of:
storing a plurality of temperature phase shift values in a table, wherein each temperature phase shift value corresponds to a temperature of the substrate;
transmitting a transmitter signal to generate a vibrational wave;
propagating the vibrational wave to vibrate the substrate;
detecting the vibrations of the substrate;
convening the vibrations into a receiver signal;
sensing the temperature of the substrate;
retrieving the temperature phase shift value corresponding to the sensed temperature of the substrate from the table;
determining a temperature phase shift attributable to the temperature of the substrate based on the temperature phase shift value; and
determining the amount of moisture on the surface based on the phase shift between the transmitter signal and the receiver signal while compensating for the temperature phase shift attributable to the temperature of the substrate.

20. A method as set forth in claim 19 further including a wiper system and further including a step of actuating the wiper system in response to the amount of moisture to remove the moisture from the surface of the substrate.

21. A method as set forth in claim 20 wherein the wiper system includes a plurality of operating levels and wherein said step of actuating includes varying the operating level of the wiper system in response to the amount of moisture on the surface.

22. A method as set forth in claim 21 wherein step of varying is further defined as increasing the operating level of the wiper system in response to the amount of moisture on the surface.

23. A method as set forth in claim 21 wherein said step of varying is further defined as decreasing the operating level of the wiper system a in response to the amount of moisture on the surface.

24. A method as set forth in claim 19 further including a step of disabling the wiper system in response to the amount of moisture on the surface.

* * * * *